United States Patent [19]

Gilman, Jr. et al.

[11] 4,232,121

[45] Nov. 4, 1980

[54] PROCESS FOR SELECTING METHINE DYES WHICH INHIBIT CELL GROWTH

[75] Inventors: Paul B. Gilman, Jr.; Robert T. Belly; Thaddeus D. Koszelak; Seymour Zigman, all of Rochester, N.Y.

[73] Assignee: Eastman Kodak Company, Rochester, N.Y.

[21] Appl. No.: 945,275

[22] Filed: Sep. 25, 1978

[51] Int. Cl.$^3$ .............................................. C12Q 1/18
[52] U.S. Cl. ...................................... 435/32; 422/28; 422/32; 435/4; 435/29; 435/240; 435/241; 435/317
[58] Field of Search ................... 435/32, 33, 4, 240, 435/241, 317, 29, 173; 422/28, 32

[56] References Cited

PUBLICATIONS

Eastman Kodak Company Annual Report for 1976, p. 23, Mar. 1977.
Mary A. Ingraham, the Bacteriostatic Action of Gentian Violet, Journal of Bacteriology, vol. 26, pp. 573-598, 1933.
Annals of New York Academy of Sciences, vol. 30, pp. 108, 117-119 (1948-1949).
Brooker et al., Science, May 9, 1947.
Experimental Chemotherapy, R. J. Schintzer and F. Hawking, ed. pp. 842-844 and 905-906 (1963).
Banno et al., Yakugaku Kenkyu, vol. 25, pp. 722-733, 1953.
Banno, Kanko Shikiso, vol. 34, pp. 1-22, 1955.
Biochemical and Biophysical Research Communications, vol. 72, No. 3, pp. 824-829, 1976.
Science, Apr. 30, 1976, Eastman Kodak Advertisement.
Scientific American, May 1976, Eastman Kodak Advertisement.
The Biological Bulletin, vol. 153, No. 2, pp. 451-452, Oct. 1977.

*Primary Examiner*—Robert J. Warden
*Attorney, Agent, or Firm*—Joshua G. Levitt

[57] ABSTRACT

Methine dyes which inhibit cell growth are identified by (1) determining the reduction potential of the dye, (2) determining the ability of the dye to sorb to the cells and (3) selecting those dyes which have a reduction potential more negative than about −0.8 volt and which are sorbed to the cells.

11 Claims, No Drawings

PROCESS FOR SELECTING METHINE DYES WHICH INHIBIT CELL GROWTH

This invention relates to a process for selecting methine dyes which will inhibit cell growth.

Methine dyes (also referred to as methylidyne dyes) comprise a methine chain (i.e., a chain of carbon atoms with alternating double and single bonds) terminated at each end with a hetero atom. The terminal hetero atoms are typically nitrogen or oxygen atoms in various combinations, and generally they are contained in or attached to an unsaturated cyclic nucleus. Typical methine dyes are cyanine dyes, merocyanine dyes and oxonol dyes.

These dyes have found wide use in photography and related arts where they are employed, inter alia, as spectral sensitizers. The dyes are used to extend the spectral response of silver halide and other photosensitive materials to regions of the spectrum where they do not have inherent or native sensitivity.

In connection with investigations of the way methine dyes function in photographic materials, a large amount of data have been generated on the reduction and oxidation potentials of methine dyes. These investigations have indicated that reduction and oxidation potentials influence the ability of methine dyes to spectrally sensitize silver halide and other light sensitive materials.

From time to time, investigations have been conducted into the effect of methine dyes in various biological systems. For example, certain methine dyes have been found to be useful as antifilarial and antithelmintic agents. [See Brooker et al, *Science*, May 9, 1947; Annals New York Academy of Sciences, Vol. 50, pp. 108, 117–9 (1948-9); and Experimental Chemotherapy, R. J. Schintzer and F. Hawking, ed., pp. 842–4, 905–6 (1963).] Subsequently, other workers have conducted investigations into the biological and, in particular, the antibacterial activity of methine dyes. This work is summarized by Banno et al in Yakugaku Kenkyu, Vol. 25, pp. 722–733 (1953) and by Banno in Kanko Shikiso, Vol. 34, pp. 1–22 (1955). These investigators attempted to predict biological activity by correlating it with the structure of dyes, including substitution on dyes.

Although an early investigator attempted to correlate the bacteriostatic action of gentian violet (not a methine dye) with its oxidation-reduction potential (see Ingraham, Journal of Bacteriology, Volumn 26, pages 573–598, 1933) and more recently the effect of reduction potential of various nitro compounds on mannalian cell toxicity has been studied (See Biochemical and Biophysical Research Communications, Volumn 72, No. 3, pages 824–829, 1976), redox potential of methine dyes and its relation to the biological activity of these dyes, has not been investigated, to out knowledge, until one of us considered such work based on experience with silver halide photography (see *Science*, April 30, 1976 and *Scientific American*, May 1976, and Eastman Kodak Company Annual Report for 1976, page 23, published March 1977).

We have found a process, employing reduction potential, which can be used to differentiate between those dyes which inhibit cell growth and those which do not. This process can be employed to select dyes which are to be used to inhibit cell growth.

In one aspect this invention comprises a process for selecting methine dyes which inhibit cell growth, the process comprising (1) determining the reduction potential ($E_R$) of the dye, (2) determining the ability of the dye to sorb to the cells to be inhibited and (3) selecting those dyes which have a reduction potential more negative than about $-0.8$ volt and which sorb to the cells. Preferably, the dye selected has a reduction potential more negative than $-1.0$ volt.

The process of the present invention can be used to select dyes which inhibit growth of both procaryotic and eucaryotic cells and cells of single-celled or multicelled organisms. The process is particularly effective for selecting dyes which inhibit cell growth in microbes, especially bacteria.

In the practice of this invention the reduction potential of a given dye can be determined in various ways. Reduction potentials for numerous methine dyes are available in the literature. If available, the published reduction potential can be employed. If a published reduction potential is not available, suitable techniques for measuring reduction potential are available and can be used. A preferred technique for measuring reduction potentials for use in accordance with this invention is the technique described in R. J. Cox, *Photographic Sensitivity*, Chapter 15, Academic Press, 1973. This technique involves measurement at 20° C., of an approximately $10^{-4}$ molar solution of the dye in an electrolyte, such as methanol which is 0.05 molar in lithium chloride, using a dropping mercury electrode. The potential values are reported by reference to a silver-silver chloride electrode in a saturated solution of potassium chloride at 20° C. Plus and minus signs are assigned to the potential values according to the IUPAC Stockholm Convention, 1953.

The ability of a given methine dye to sorb to specific cells can be determined readily by several techniques. If the cells are of a size which can be visually observed, with or without the aid of a light microscope, a solution of the dye in an appropriate solvent, e.g., methanol, can be brought into contact with the cells and a determination can be made as to whether or not the cells are colored by the dye. Those dyes which color the cell are sorbed thereto.

Another technique, which is particularly effective with cells which cannot be visually observed, is to determine the amount of dye bound to the cells using spectrophotometric measurements. This can be accomplished by contacting a given concentration of the dye with the cells, removing the cells from the dye solution and then comparing the optical density (at $\lambda_{max}$) of the remaining dye solution with a control containing the original concentration of the dye. The percentage decrease in optical density indicates the percentage of dye which has been bound to the cells. This technique is described in more detail in Example 8, below. If this technique indicates that ten percent or more of the dye is bound to the cells, the dye is considered to sorb to the cells for the purposes of this invention.

Various factors may influence the ability of the given dye to sorb to given cells. These include: the presence or absence of an electrical charge on the dye and the cells and, if present, the sign of the charge on the dye relative to the sign of the charge on the cells; the solubility of the dye in water and lipids; the substituents on the dye; and the bulk and molecular weight of the dye. However, if one of the techniques described above is used to determine if the dye sorbs to the cells, these factors need not be considered, except perhaps to explain why a given dye does not sorb to the cells.

In another aspect, this invention relates to a process for inhibiting cell growth, particularly microbial cell growth, comprising selecting a dye by the process described above and then contacting the cells to be inhibited with the dye so selected.

The dye can be contacted with the cells by introducing it into the environment where the cells exist by any suitable means. To aid introduction of the dye into the environment of the cells, it is preferred that the dye be present in a non-interferring carrier. Preferably, the carrier is a liquid, such as methanol, in which the dye is soluble. The concentration of dye effective to inhibit cell growth will depend upon the activity of the particular dye selected and the susceptibility of the cells to inhibition. Generally, suitable concentrations of dye will be $10^{-6}$ molar or greater, e.g. $10-6$ to $10^{-2}$ molar.

In yet another aspect, this invention relates to a process for manufacturing a cell growth inhibitory composition comprising selecting a dye by the process described above, and then, combining the dye so selected with a non-interferring carrier. The carrier is preferably a liquid, such as methanol, in which the dye is soluble.

While the process of this invention is useful with all methine dyes, it is particularly useful with cyanine dyes. Such dyes have the nitrogen hetero atom which terminates the methine chain in a heterocyclic nucleus. Typical nuclei are quinoline, pyridine, isoquinoline, 3H-indole, benz[E]-indole, oxazole, thiazole, selenazole, imidazole, benzoxazole, benzothiazole, benzoselenazole, benzimidazole, naphthothiazole, naphthoxazole, naphthoselenazole, pyrylium and imidazolepyrizine. These nuclei are typically in the form of quaternary salts and are joined to one another by a methine chain containing an odd number of carbon atoms so that the nitrogen atoms are conjugated to one another (i.e., separated by alternating double and single bonds).

The following examples further illustrate this invention.

The methine dyes employed in the examples which follow are listed below, by structure, in order of reduction potential ($E_R$).

| Dye | $E_R$ (volts) |
|---|---|
| 1 | −1.69 |
| 2 | −1.60 |
| 3 | −1.35 |
| 4 | −1.31 |
| 5 | −1.28 |
| 6 | −1.27 |
| 7 | −1.26 |

-continued

| Dye | | $E_R$ (volts) |
|---|---|---|
| 8 | [structure: H₃OS-benzoxazole-CH=CH-CH=benzoxazole-SO₃⁻, N-Et groups] | −1.26 |
| 9 | [structure: Cl-phenyl-CH=... -CH=CH-CH=... -phenyl-Cl, N-Et groups, I⁻] | −1.18 |
| 10 | [structure: acetoxy-benzoxazole-CH=CH-CH=benzoxazole-acetoxy, N-Et groups, I⁻] | −1.17 |
| 11 | [structure: benzothiazole-CH=C(Me)-CH=benzothiazole, N-Et groups, I⁻] | −1.16 |
| 12 | [structure: naphthothiazole-C=CH-CH=CH-C=naphthothiazole, N-Et groups, PTS⁻] | −1.12 |
| 13 | [structure: dihydroquinoline-CH=CH-CH= quinoline, N-Et groups, Cl⁻] | −1.10 |
| 14 | [structure: benzothiazoline-CH=quinoline, N-Me and N-Et groups, I⁻] | −1.08 |
| 15 | [structure: Cl-benzothiazole-C=CH-C(Et)=C-benzothiazole-Cl, N-Et groups, Br⁻] | −1.06 |
| 16 | [structure: quinoline-CH=CH=quinoline, N-Et groups, Br⁻] | −1.03 |
| 17 | [structure: benzothiazole-C=CH-CH=CH-C-benzothiazole, N-Et groups, I⁺] | −1.00 |
| 18 | [structure: HC-benzoxazole-C=CH-CH=CH-C-benzoxazole-CH, N-CH₃ groups, FSO₃⁻] | −0.99 |

-continued

| Dye | | $E_R$ (volts) |
|---|---|---|
| 19 | [structure: bis-naphthothiazole trimethine cyanine, N-Et, N-Et, PTS⁻] | −0.90 (calculated) |
| 20 | [structure: bis(5-chlorobenzothiazole) trimethine cyanine, N-Et, N-Et, PTS⁻] | −0.86 |
| 21 | [structure: bis-benzoxazole pentamethine cyanine, N-Et, N-Et, ClO₄⁻] | −0.83 |
| 22 | [structure: bis-benzothiazole pentamethine cyanine, N-Et, N-Et, I⁻] | −0.83 |
| 23 | [structure: bis(imidazo[4,5-b]quinoxaline) trimethine cyanine, N-Alkyl/Et, ClO₄⁻] | −0.81 |
| 24 | [structure: bis(imidazo[4,5-b]quinoxaline) trimethine cyanine, N-Et, Cl⁻] | −0.79 |
| 25 | [structure: bis(chloro-N-phenyl imidazo[4,5-b]quinoxaline) trimethine cyanine, Ph, PTS⁻] | −0.65 |
| 26 | [structure: bis-benzothiazole azamethine dye, N-Et, N-Et, I⁻] | −0.64 |
| 27 | [structure: thiazolo-quinoline / benzothiazole trimethine cyanine, N-Et, Br⁻] | −0.63 |
| 28 | [structure: 6-nitrobenzothiazole–naphthoquinolinium monomethine, N-Et, EtSO₄⁻] | −0.60 |
| 29 | [structure: 6-nitrobenzothiazole pentamethine hemicyanine with 4-nitrophenyl N-Et amine, Cl⁻] | −0.58 |

| Dye | | $E_R$ (volts) |
|---|---|---|
| 30 | 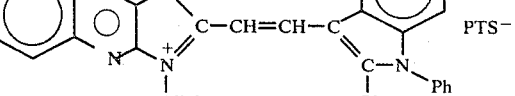 | −0.54 |
| 31 | 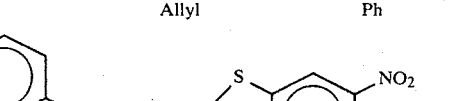 | −0.41 |
| 32 | 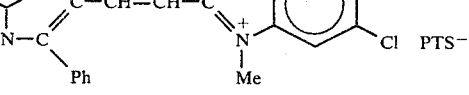 | −0.32 |
| 33 | 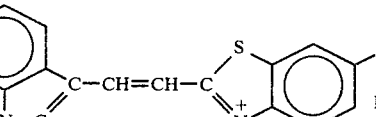 | −0.20 |
| 34 | 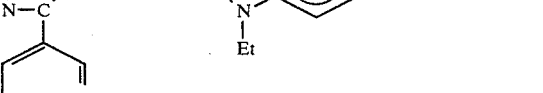 | −0.11 |

EXAMPLE 1

Effect of Reduction Potential of Cyanine Dyes Upon Inhibition of Bacterial Growth A. Preparation of *Bacillus pumilus*, strain K-1 culture in nutrient broth.

Nutrient broth was prepared by mixing 8 grams of BACTO dehydrated nutrient broth per liter of distilled water. (BACTO products are sold by the Difco Company.) The nutrient broth was sterilized in an autoclave for 20 minutes at 121° C. and 20 psi. Samples of the nutrient broth were then inoculated with *Bacillus pumilus* strain K-1 culture. The inoculated samples were then incubated at 37° C. for forty-eight hours.

B. Preparation of nutrient agar plates:

Nutrient agar was prepared by mixing 23 grams of BACTO nutrient agar per liter of distilled water. The nutrient agar was sterilized in the same way as the nutrient broth. After it has cooled to about 45° C. 250 ml of the nutrient agar solution was aeseptically inoculated with 5 ml of the *Bacillus pumilus*, K-1 culture prepared in (A), above. Plates of the inoculated nutrient agar were then poured and allowed to harden.

C. Preparation of dye solutions and addition of dyes to the inoculated agar plates:

Cyanine dye solutions in methanol or methanol:water were prepared at $10^{-4}$ molar concentration. To minimize possible photocatalyzed reactions of the dyes, all preparations were performed under yellow lights and all incubations were performed in the dark.

Schleider and Schuell #740-E filter paper (12.7 mm diameter) was dipped in the dye solution, touched to the side of the beaker to removed excess dye, and placed in the center of the inoculated agar plates (prepared in (B) above). The plates were then incubated at 26° C. for fifty hours. The plates were then examined to determine if bacterial growth had been affected by the dye-containing filter paper. With certain dyes bacterial growth was inhibited in a circular area around the filter paper. The diameter of that circle is reported in Table I, below. With other dyes no such area of inhibition was observed. This is reported in Table I, below.

TABLE I

| Dye | $E_R$ | $E_{ox}$ | Culture | Diameter of Inhibition |
|---|---|---|---|---|
| 3 | −1.35 | + .54 | Bacillus K-1 | 18.5 mm |
| 7 | −1.26 | + .94 | " | 22.5 mm |
| 33 | − .20 | >+1.00 | " | None |
| 34 | − .11 | >+ .91 | " | None |

EXAMPLE 2

Effect of Reduction Potential of Cyanine Dyes Upon Inhibition of Bacterial Growth Example 1 was repeated except that the plates were incubated for forty-eight hours. The correlation between diameter of inhibition and reduction potential of the dye is listed in Table II, below

TABLE II

| Dye | $E_R$ | $E_{ox}$ | Diameter of Inhibition |
|---|---|---|---|
| 2 | −1.60 | | None |
| 3 | −1.35 | + .54 | 19 mm |
| 7 | −1.26 | + .94 | 25.5 mm |
| 11 | −1.16 | | 18 mm |
| 13 | −1.10 | | slight |
| 14 | −1.08 | | 15 mm |
| 15 | −1.06 | + .87 | 13.5 mm |
| 16 | −1.03 | + .99 | 25.5 mm |
| 17 | −1.00 | + .78 | 16.5 mm |
| 22 | − .83 | | 15 mm |
| 24 | − .79 | +1.00 | None |
| 26 | − .64 | > +1.00 | 14.5 mm |
| 27 | − .63 | > +1.00 | None |
| 28 | − .60 | | None |
| 31 | − .41 | > +1.00 | None |
| 32 | − .32 | > +1.00 | None |
| 33 | − .20 | > +1.00 | None |
| 34 | − .11 | > +.91 | None |

As can be seen in Table II, there is generally good agreement between reduction potential and the ability of the dyes to inhibit bacterial growth. Dyes with reduction potentials of −0.8 e.v. and more negative inhibited the growth of the bacteria.

EXAMPLE 3

Effect of Oxidation Potential of Cyanine Dyes Upon Inhibition of Bacterial Growth As can be seen from Tables I and II, there is little or no correlation between the oxidation potential ($E_{ox}$) of a dye and its ability to inhibit the growth of the bacteria.

EXAMPLE 4

Effect of Light

Example 2 was repeated except that duplicate sets of plates were prepared and one set was incubated under white light at 26° C. for twenty-seven hours, while the other set was incubated in the dark at the same temperature and for the same time. No significant difference in inhibitory effect of a given dye was observed as a result of the presence or absence of light. Dyes that inhibited growth under white light conditions also inhibited growth in the dark. Conversely, dyes that did not inhibit growth under white light also did not inhibit growth in the dark. Although in some instances there were slight differences in the diameter of inhibition for any one dye, light vs. dark, the overall conclusion is that excitation of the dye by light is not involved in the inhibition of growth by these dyes.

EXAMPLE 5

Effect of Concentration of Cyanine Dye Upon Inhibition of Bacterial Growth

Example 1 was repeated except that Dye 7 was employed at varying concentrations and compared with an aqueous phenol solution at varying concentrations. The concentrations and diameters of inhibition is shown in Table III.

TABLE III

| Compound | Concentration | Diameter of Inhibition |
|---|---|---|
| Dye 7 | $2.5 \times 10^{-5}$M | 14.5 mm |
| Dye 7 | $5.0 \times 10^{-5}$M | 20 |
| Dye 7 | $1.0 \times 10^{-4}$M | 26 |
| Dye 7 | $2.0 \times 10^{-4}$M | 29 |
| Phenol | $2.13 \times 10^{-1}$M | 26 |
| Phenol | $1.06 \times 10^{-1}$M | 22 |
| Phenol | $0.53 \times 10^{-1}$M | 18 |

As can be seen in Table III, an increase in concentration of Dye 7 results in a corresponding increase in the diameter of inhibition. Also, dye 7 at $1 \times 10^{-4}$ molar concentration gave the same degree of inhibition as phenol at $2.13 \times 10^{-1}$ molar. This would indicate that dye 7 is potentially 2000 times more active as an inhibitor than phenol.

EXAMPLE 6

Effect of Varying the Anion of the Dye

Example 1 was repeated except Dye 17 with differing anions was employed at a concentration of $10^{-3}$ molar and the plates were incubated for three days. The results are given in Table IV. As can be seen, there is no effect upon diameter of inhibition as a result of changing the anion.

TABLE IV

| Dye | Anion | Diameter of Inhibition |
|---|---|---|
| 17 | $ClO_4^-$ | 19 mm |
| 17 | $Br^-$ | 19 mm |
| 17 | $I^-$ | 19 mm |
| 17 | $PTS^-$ | 19 mm |

EXAMPLE 7

Effect of Varying the Substituents on Cyanine Dyes

Example 6 was repeated except that Dyes 7 and 17 unsubstituted and substituted with various electron withdrawing or electron donating groups were employed. Electron withdrawing groups tend to lower the reduction potential of the dye (i.e., make it less negative) while electron donating groups tend to raise the reduction potential of the dye (i.e., make it more negative). The dyes, the substituents and the diameter of inhibition is reported in Tables V and VI, below. These tables also indicate whether a substituent is electron withdrawing (w) or electron donating (d) and, where measured, the reduction and oxidation potentials of the dyes.

TABLE V

| Dye | Substituent | | $E_R$ | $E_{ox}$ | Diameter of Inhibition |
|---|---|---|---|---|---|
| 17 | Unsubstituted | | −1.00 | 4.75 | 19 mm |
| | 7,7'-dimethylamino | (d) | | | 14 |
| | 6,6'-diamino-N,N'-dimethyl | (d) | | | None |
| | 6,6'-dihydroxy | (d) | | | 15.5 |
| | 4,4'-dimethoxy | (d) | | | 17.5 |
| | 5,5'-dimethoxy | (d) | | | 14.5 |
| | 5,5',6,6'-tetramethoxy | (d) | | | None |
| | 6,6'-dimethoxy | (d) | | | 15 |
| | 7,7'-dimethoxy | (d) | | | 14.5 |
| | 6,6'-diethoxy | (d) | | | 15 |
| | 6,6'-dimethyl | (d) | | | 15 |
| | 6,6'-diacetamido | (w) | | | None |
| | 6,6'-difluoro | (w) | −1.06 | | 18 |
| | 6,6'-disulfo | (w) | | | None |
| | 6,6'-dichloro- | (w) | −.87 | | 14 |
| | 6,6'-dibromo | (w) | −.88 | | None |

TABLE V-continued

| Dye | Substituent | | $E_R$ | $E_{ox}$ | Diameter of Inhibition |
|---|---|---|---|---|---|
| | 6.6'-diiodo | (w) | −.84 | | None |
| | 6,6'-diacetoxy | (w) | | | 17 |
| | 5,5'-diacetoxy | (w) | | | 15 |
| | 6,6'-dicyano-N,N'-dimethyl | (w) | | | None |
| | 6,6'-dinitro | (w) | −.58 | +.96 | None |
| | 5,5'-dichloro | (w) | −.86 | +.85 | 14 |
| | 5,5'-dibromo | (w) | | | 13.5 |
| | 5,5'-dimethyl | (d) | | | 14 |

TABLE VI

| Dye | Substituent | | $E_R$ | $E_{ox}$ | Diameter of Inhibition |
|---|---|---|---|---|---|
| 7 | Unsubstituted | | −1.26 | +.94 | 34 mm |
| | 4,4'-dihydroxy | (d) | | | 13 |
| | 5,5'-dihydroxy | (d) | | | 14 |
| | 5,5'-dimethoxy | (d) | | | 23.5 |
| | 6,6'-dimethoxy | (d) | −1.31 | +.84 | 28.5 |
| | 5,5'-diethoxy | (d) | | | 14 |
| | 6,6'-diethoxy | (d) | | | 16 |
| | 5,5'-dimethyl | (d) | −1.28 | +.96 | 27 |
| | 5,5'-diethyl | (d) | | | 23 |
| | 5,5'-diphenyl | (w) | | | None |
| | 6,6'-diphenyl | (d) | | | None |
| | 7,7'-diphenyl | (w) | | | None |
| | 5,5'-dicarboxy-N,N'-methyl | (w) | | | None |
| | 5,5'-acetamido | (w) | | | None |
| | 5,5'-disulfo | (w) | −1.27 | | None |
| | 6,6'-disulfo | (w) | −1.26 | +1.00 | None |
| | 5,5'-dichloro | (w) | | | 26.5 |
| | 6,6'-dichloro | (w) | −1.17 | +1.07 | 28.5 |
| | 5,5'-dibromo | (w) | | | 22.5 |
| | 4,4'-diacetoxy | (w) | | | 15 |
| | 5,5'-diacetoxy | (w) | −1.18 | | 30.5 |
| | 5,5'-dicyano-N,N'-methyl | (w) | −.99 | | None |
| | 5,5'-dinitro-N,N'-methyl | (w) | | | None |
| | 6,6'-dinitro-N,N'-methyl | (w) | | | None |

EXAMPLE 8

Binding of Dyes to Bacteria

A culture of *Bacillus pumilus* (K-1) was grown for twenty-four hours in the nutrient broth of Example 1 with agitation at 28° C. The culture was collected by centrifugation at 5,000×g. for 10 minutes, and the resultant pellet was washed several times in cold 0.05 M potassium phosphate buffer, pH 7.0. The pellet was resuspended in the buffer solution to a final optical density of 1.0 at 620 nm as measured with a Bausch and Lomb Spectronic 20.

One-tenth ml of dye solution (1 mg/ml in methanol) was added to a tube containing 5 ml of cell suspension described above and a control tube containing 0.05 M potassium phosphate buffer, pH 7.0. All tubes were well agitated using a Vari-Whirl Mixer (Will Scientific Co.) and then centrifuged at 10,000×g. for 10 minutes. The visible spectrum of either the undiluted supernatant or a dilution of supernatant (usually 0.5 ml to 2.5 ml buffer solution) was determined by means of a Perkin-Elmer 572 spectrophotometer (1.0 nm slit) against a blank cuvette containing buffer solution.

The percent binding of dye to the cells for each dye, was determined by comparison of the density at $\lambda_{max}$ of the control supernatant sample with the density at $\lambda_{max}$ of the supernatant of the cell sample. The percentage of dye bound is given in Table VII.

TABLE VII

| Dye | $E_R$ | % Bound |
|---|---|---|
| 3 | −1.35 | 11.2 |
| 7 | −1.26 | 31.7 |
| 12 | −1.12 | 93.1 |
| 15 | −1.06 | 74.9 |
| 16 | −1.03 | 28.7 |
| 17 | −1.00 | 73.1 |
| 19 | −0.90 | 100 |
| 20 | −0.86 | 76.3 |
| 23 | −0.81 | 0 |
| 24 | −0.79 | 32.8 |
| 25 | −0.65 | 92.6 |
| 26 | −0.64 | 56.3 |
| 30 | −0.54 | 88.2 |
| 31 | −0.41 | 54.2 |
| 32 | −0.32 | 61.0 |
| 33 | −0.20 | 83.7 |
| 34 | −0.11 | 75.0 |

EXAMPLE 9

Effect of Cyanine Dyes on Various Bacteria

Cultures of various gram-negative and gram-positive bacteria were prepared in nutrient and Tryptic Soy Agar and plates were poured as described in Example 1. Methanolic solutions of cyanine dyes were prepared at $10^{-3}$ molar and applied to the plates using the filter paper technique described in Example 1. Control plates were prepared in which the filter paper contained methanol or a 0.2 molar aqueous solution of phenol. The plates were then incubated at 26° C. or 37° C. for forty-eight hours. The bacteria, growth broth medium, dyes, time of incubation and diameter of inhibition are reported in Table VIII.

TABLE VIII

Effect of Spectral Sensitizers on Various Gram-Negative and Gram-Positive Bacteria

| Organism | Gram ± | Broth | Incubation Temp/Time | Area of Inhibition Spectral Sensitizer | | | | | Control | |
|---|---|---|---|---|---|---|---|---|---|---|
| | | | | #17 | #7 | #1 | #21 | #24 | #33 | MeOH | 0.2 M Phenol |
| *Bacillus pumilus* (K-1) | + | Nutrient | 37° C./48 hrs | 17mm | 24mm | 18mm | 21mm | 13mm | No | No | 22mm |
| *Proteus vulgaris* | − | " | 37° C./48 hrs | No | No | No | No | No | No | No | No |
| *Escherichia coli,* Strain B | − | " | 37° C./48 hrs | No | No | No | No | No | No | No | No |
| *Micrococcus flavus* | + | " | 26° C./48 hrs | 15mm | 19mm | No | 18mm | 13mm | No | No | 16mm |
| *Bacillus megaterium* | + | Tryptic Soy | 37° C./48 hrs | 14mm | 21mm | 17mm | 18mm | 14mm | No | No | Slight |
| *Enterobacter aerogenes* | − | " | 37° C./48 hrs | No | No | No | No | Slight | No | No | No |
| *Alcaligenes faecalis* | − | " | 37° C./48 hrs | No | No | No | No | No | No | No | 15mm |
| *Bacillus cereus* | + | " | 26° C./48 hrs | 13mm | 14mm | No | 14mm | 13.5mm | No | No | 14mm |
| *Micrococus luteus* | + | " | 26° C./48 hrs | 14mm | 16mm | 22mm | 14mm | 14mm | Slight | No | 15mm |

TABLE VIII-continued

Effect of Spectral Sensitizers on Various Gram-Negative and Gram-Positive Bacteria

| Organism | Gram ± | Broth | Incubation Temp/Time | Area of Inhibition Spectral Sensitizer | | | | | | Control | 0.2 M |
|---|---|---|---|---|---|---|---|---|---|---|---|
| | | | | #17 | #7 | #1 | #21 | #24 | #33 | MeOH | Phenol |
| *Bacillus subtilis* | + | " | 26° C./48 hrs | 15mm | 18mm | 13mm | 16mm | 13mm | 13mm | No | 13mm |

As can be seen, the dyes inhibited growth of gram-positive bacteria, but did not inhibit growth of gram-negative bacteria at the concentrations tested. In addition, binding of dyes 7, 17 and 24 to the bacteria was determined as in Example 8. All of the dyes were found to bind.

EXAMPLE 10

Percent binding of various dyes to *Bacillus pumilus* (K-1) was determined by the procedure of Example 8. This is reported in Table IX, below. Also reported in this table is the diameter of inhibition of various dyes at two different concentrations. This data is taken from previous examples herein or was obtained by the same procedure. Each dye for which diameter of inhibition data is presented was rated for activity relative to the concentration of an aqueous phenol solution necessary to give an equal diameter of inhibition. Dye 7 for which data is reported in Example 5 was given an arbitrary rating of 100 and the other dyes are reported relative to it on a linear scale except for dye 20 which was rate relative to dye 17. The activity ratings are reported in Table IX below. In addition Table IX reports the activity of the dyes as inhibitors of cell division in sea urchins. Activity was rated on an arbitrary scale from 0 to 5; 5 being the most active. This data was generated as follows:

To suspensions in filtered sea water of fertilized sea urchin eggs there was added, three minutes after fertilization, methanolic solutions of the dyes in an amount sufficient to yield a final concentration of dye of between $10^{-5}$ and $10^{-6}$ molar. The final concentration of methanol was, at a maximum $1 \times 10^{-4}$ molar. The eggs were visually observed at 60 minutes after fertilization to determine if cell division and the formation of mitotic apparatus had been inhibited. A rating was assigned based on the concentration of dye required to inhibit cell division and synthesis of DNA. The more active dyes (i.e., those with higher number ratings) inhibited at lower concentrations.

From Table IX it will be observed that to inhibit growth the dye must be bound to cells. Anionic dyes, which are poorly bound to bacteria due to the negative charge at the surface of the cells, did not inhibit. It will also be observed that at a given concentration, dyes with more negative reduction potentials tend to be more active inhibitors.

TABLE IX

*Bacillus pumilus* K-1

| Dye | $E_R$ | % Bound | Diameter of Inhibition $10^{-4}$M | $10^{-3}$M | Activity Rating $10^{-4}$M | $10^{-3}$M | Comment | Sea Urchin Eggs Activity |
|---|---|---|---|---|---|---|---|---|
| 1 | −1.69 | 33.6 | | 18 mm | | 39 | | |
| 2 | −1.60 | 31.8 | None | None | 0 | 0 | Large molecule, | |
| 3 | −1.35 | 11.2 | 19 mm | | 29 | | | +5 |
| 4 | −1.31 | 97.2 | | 28.5 | | 71 | | +4 |
| 5 | −1.28 | 97.6 | | 27 | | 65 | | +4 |
| 6 | −1.27 | 3.3 | | None | | 0 | Anionic, low binding | |
| 7 | −1.26 | 31.7 | 25.5 | 34 | 100 | 100 | | +4 |
| 8 | −1.26 | 2.6 | | None | | 0 | Anionic, low binding | |
| 9 | −1.18 | 95.1 | | 30.5 | | 71 | | |
| 10 | −1.17 | 68.8 | | 28.5 | | 80 | | |
| 11 | −1.16 | 98.9 | 18 | | 25 | | | |
| 12 | −1.12 | 93.1 | | | | | Insoluble | 0 |
| 13 | −1.10 | 1.25 | | | | | Not Completely Soluble, low binding | |
| 14 | −1.08 | 58.3 | 15 | | 11 | | | |
| 15 | −1.06 | 74.9 | 13.5 | | 04 | | | +4 |
| 16 | −1.03 | 28.7 | 25.5 | | 100 | | | +5 |
| 17 | −1.00 | 73.1 | 16.5 | 19 | 18 | 31 | | +4 |
| 18 | −.99 | | | | | | Not Completely Soluble | 0 |
| 19 | −.90 | 100 | | | | | Dye Reacted With Agar | 0 |
| 20 | −.86 | 76.3 | | 14 | | 9 | | +3 |
| 21 | −.83 | 99.4 | | 21 | | 66 | | |
| 22 | −.83 | 98.4 | 15 | | 11 | | | |
| 23 | −.81 | 0 | | | | | Dye Reacted With Agar, Not Bound | 0 |
| 24 | −.79 | 32.8 | None | 13 | 0 | 2 | | 0 |
| 25 | −.65 | 92.6 | | | | | Dye Color Change, Solubility Problem | 0 |
| 26 | −.64 | 56.3 | 14.5 | | 8 | - | | +2 |
| 27 | −.63 | | None | | 0 | | | 0 |

TABLE IX-continued

| | | | Bacillus pumilus K-1 | | | | | |
| | | | Diameter of Inhibition | | Activity Rating | | | Sea Urchin Eggs |
| Dye | $E_R$ | % Bound | $10^{-4}$M | $10^{-3}$M | $10^{-4}$M | $10^{-3}$M | Comment | Activity |
|---|---|---|---|---|---|---|---|---|
| 28 | −.60 | 57.3 | None | | 0 | | | |
| 29 | −.58 | 67.9 | | None | | 0 | | 0 |
| 30 | −.54 | 88.2 | | | | | Insoluble | 0 |
| 31 | −.41 | 54.2 | None | | 0 | | | 0 |
| 32 | −.32 | 61.0 | None | | 0 | | | +2 |
| 33 | −.20 | 83.7 | None | None | 0 | 0 | | 0 |
| 34 | −.11 | 75.0 | None | | 0 | | | 0 |

This invention has been described in detail with particular reference to preferred embodiments thereof, but it will be understood that variations and modifications can be effected within the spirit and scope of the invention.

What is claimed is:

1. A process for selecting methine dyes which inhibit cell growth, the process comprising (1) determining the reduction potential ($E_R$) of the dyes, (2) determining the ability of the dyes to bind to the cells and (3) selecting those dyes which have a reduction potential more negative than about −0.8 volt and which bind to the cells to the extent of 10% or greater.

2. A process of claim 1 wherein the dyes selected have a reduction potential more negative than about −1.0 volt.

3. A process of claim 1 wherein the dyes selected are cyanine dyes.

4. A process of claim 1 wherein the dyes are selected to inhibit the growth of procaryotic cells.

5. A process of claim 1 wherein the dyes are selected to inhibit the growth of eucaryotic cells.

6. A process for inhibiting cell growth comprising the steps of:

(1) selecting a dye by the process of claim 1, and
(2) contacting the cells to be inhibited with the selected type.

7. A process for manufacturing a cell growth inhibitory composition comprising the steps of:

(1) selecting a dye by the process of claim 1, and
(2) combining the selected dye with a non-interfering carrier.

8. A process for selecting antimicrobial methine dyes, the process comprising (1) determining the reduction potential ($E_R$) of the dyes, (2) determining the ability of the dyes to bind to the cells of the microbes and (3) selecting an antimicrobial agents those dyes which have a reduction potential more negative than about −0.8 volt and which bind to the microbial cells to the extent of 10% or greater.

9. A process of claim 8 wherein the dyes selected have a reduction potential more negative than about −1.0 volt.

10. A process of claim 8 wherein the dyes selected are cyanine dyes.

11. A process of claim 8 wherein the dyes are selected to inhibit the growth of bacteria.

* * * * *